United States Patent [19]

Nojima et al.

[11] Patent Number: 4,649,203

[45] Date of Patent: Mar. 10, 1987

[54] KETOALKYLPHOSPHOLIPIDS

[75] Inventors: Shoshichi Nojima, Tokyo; Hiroaki Nomura; Susumu Tsushima, both of Osaka, all of Japan

[73] Assignee: Takeda Chemical Industries, Ltd., Osaka, Japan

[21] Appl. No.: 843,811

[22] Filed: Mar. 27, 1986

Related U.S. Application Data

[63] Continuation of Ser. No. 659,928, Oct. 11, 1984, abandoned.

[30] Foreign Application Priority Data

Oct. 11, 1983 [JP] Japan .................................. 58-190349

[51] Int. Cl.$^4$ ............................. C07F 9/10; C07F 9/65
[52] U.S. Cl. ................................... 548/112; 544/157; 544/232; 544/337; 546/22; 546/23; 558/169
[58] Field of Search ....................... 544/157, 232, 337; 546/22, 23; 548/112; 558/169

[56] References Cited

U.S. PATENT DOCUMENTS

| | | | |
|---|---|---|---|
| 4,329,302 | 5/1982 | Hanahan et al. | 260/925 |
| 4,408,052 | 10/1983 | Hozumi et al. | 546/22 |
| 4,426,525 | 1/1984 | Hozumi et al. | 546/22 |
| 4,492,659 | 1/1985 | Bosies et al. | 260/925 |

FOREIGN PATENT DOCUMENTS

| | | |
|---|---|---|
| 772649 | 2/1978 | South Africa . |
| 1575545 | 9/1980 | United Kingdom . |

OTHER PUBLICATIONS

Central Patent Index Basic Abstracts Journal: Section B: Farmdoc; 10077 K/05 B05 BOEF 11.07.81 EP-6-9-968.

*Primary Examiner*—Richard L. Raymond
*Attorney, Agent, or Firm*—Wegner & Bretschneider

[57] ABSTRACT

Novel ketoalkylphospholipids, inclusive of salts thereof, of the formula

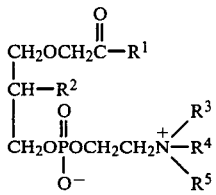

wherein
R$^1$ is an aliphatic hydrocarbon residue containing 10 to 20 carbon atoms,
R$^2$ is hydrogen or methoxy, and
R$^3$, R$^4$ and R$^5$ are independently hydrogen or C$_{1-5}$ alkyl, or

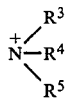

represents a cyclic ammonio group, exhibit inhibitory activity against multiplication of tumor cells and antifungal activity.

16 Claims, No Drawings

KETOALKYLPHOSPHOLIPIDS

This application is a continuation of application Ser. No. 659,928, filed 10/11/84, now abandoned.

This invention relates to ketoalkylphospholipids. More particularly, this invention relates to compounds of the formula

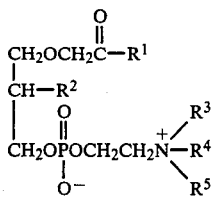
(I)

wherein
$R^1$ is an aliphatic hydrocarbon residue containing 10 to 20 carbon atoms,
$R^2$ is hydrogen or methoxy, and
$R^3$, $R^4$ and $R^5$ are independently hydrogen or $C_{1-5}$ alkyl, or

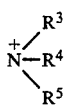

represents a cyclic ammonio group,
or pharmaceutically acceptable salts thereof.

Referring to the above formula (I), the aliphatic hydrocarbon residue containing 10 to 20 carbon atoms represented by $R^1$ may be straight or branched and may be saturated or unsaturated, and thus includes, among others, $C_{10-20}$ alkyl groups [e.g. n-decyl, n-dodecyl, n-tridecyl, n-tetradecyl, n-pentadecyl, n-hexadecyl, n-octadecyl, 3,7,11-trimethyldodecyl, 3,7,11,15-tetramethylhexadecyl], $C_{10-20}$ alkenyl groups [e.g. 7-dodecenyl, 8-tridecenyl, 8-tetradecenyl, 5-pentadecenyl, 6-hexadecenyl, 1-heptadecenyl, 10-heptadecenyl, 8,11-octadecadienyl, 3,7,11-trimethyl-2,6,10-tridecatrienyl, 3,7,11,15-tetramethyl-2,6,10,14-hexadecatetraenyl] and $C_{10-20}$ alkynyl groups [e.g. 4-tridecynyl, 6-pentadecynyl, 7-hexadecynyl, 9-octadecynyl, 6,12-pentadecadiynyl, 7,13-hexadecadiynyl, 9,15-octadecadiynyl]. Said alkenyl groups may have either the Z configuration or the E configuration. The above-mentioned groups may have a substituent or substituents such as hydroxyl, mercapto, amino, oxo, carbamoyl, carboxyl, halogen, $C_{3-7}$ cycloalkyl, phenyl and other groups.

The $C_{1-5}$ alkyl group represented by $R^3$, $R^4$ or $R^5$ includes, for example, methyl, ethyl, propyl, butyl or pentyl.

As the cyclic ammonio group represented by

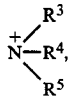

there may be mentioned a pyridinio group, an oxazolio group, a thiazolio group, a pyridazinio group, a quinolinio group, an isoquinolinio group, etc., and these groups may have a substituent or substituents such as $C_{1-4}$ alkyl (e.g. methyl, ethyl, propyl, butyl), hydroxyl, hydroxyethyl, aminoethyl, amino (imino), carbamoyl, ureido and other groups. The above cyclic ammonio group also includes those cases in which two of $R^3$, $R^4$ and $R^5$ form a ring together with the quaternary nitrogen atom and the remaining one is, for example, $C_{1-4}$ alkyl (e.g. methyl, ethyl, propyl, butyl), more specifically, the cases where there is formed an N-methylmorpholinio group or an N-methylpiperazinio group, for instance.

When $R^2$ is a methoxy group, two stereoisomers, one having the R configuration and the other having the S configuration, can occur for each compound (I). The present invention covers the respective stereoisomers as well as mixtures thereof and the racemate.

The compounds (I) may occur in the salt representable, for instance, by the formula

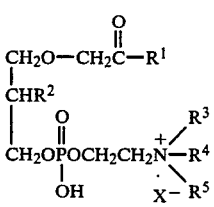
(Ia)

wherein $X^-$ is an anion such as a chloride, bromide or iodide ion and other symbols are as defined above, or by the formula

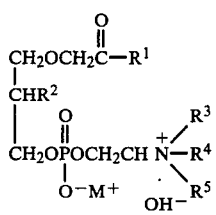
(Ib)

wherein $M^+$ is an alkali metal (e.g. Na, K) ion or an alkaline earth metal (e.g. Ca, Mg) ion and other symbols are as defined above. In that case, pharmaceutically acceptable salts are preferred.

The compounds (I) of the present invention can be produced, for example, by the following processes:

Process A

2-O-Methylglycerol (II) [synthesized by the method described in J. Chem. Soc., 1934, 1234 or Ann., 709, 2421 (1967)] or 1,3-propanediol (II') is derived to a compound of the formula

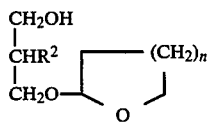
(III)

wherein $R^2$ is as defined above and n is an integer of 1 or 2. Then, a compound of the formula

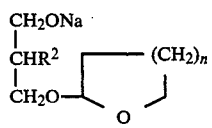
(III')

wherein each symbol is as defined above, is prepared from the compound (III) and reacted with a compound of the formula

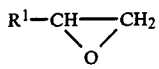 (IV)

wherein R¹ is as defined above, in an inert solvent and under the anhydrous condition. The resulting compound of the formula

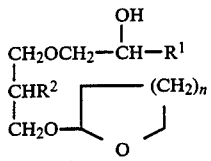 (V)

wherein each symbol is as defined above, is then treated with an oxidizing agent, followed by deprotection, whereby a compound of the formula

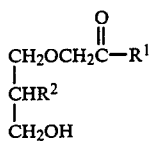 (VI)

wherein each symbol is as defined above, can be obtained.

The compound (IV) can be produced by the method of Swern [J. Am. Chem. Soc., 68, 1504 (1946)] starting from a compound of the formula

 (IV')

wherein R¹ is as defined above. Preferred oxidizing agents for oxidizing the compound (V) are chromic acid, chromic anhydride and chromyl chloride as well as adducts between these reagents and acetic acid, acetone or pyridine, for instance. The deprotection can be realized by treatment with a dilute acid.

The compound (VI) obtained in the above is reacted with a compound of the formula

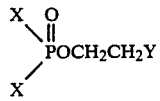 (VII)

wherein X and Y each is a halogen atom (e.g. chlorine, bromine, iodine), followed by treatment with water, which gives a compound of the formula

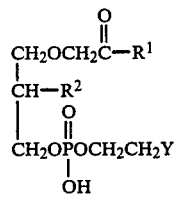 (VIII)

wherein R¹, R² and Y are as defined above. This is reacted with a compound of the formula

 (IX)

wherein the symbols are as defined above, to give the compound (I).

Process B

The compound (VI) is reacted with a compound of the formula

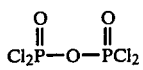 (X)

followed by treatment with water. The resulting compound of the formula

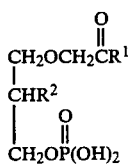 (XI)

wherein R¹ and R² are as defined above, is reacted with a compound of the formula

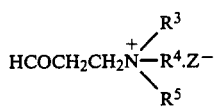 (XII)

wherein R³, R⁴ and R⁵ are as defined above and Z⁻ is an anion (e.g.

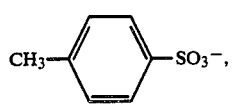

CH₃COO⁻, HO⁻, Br⁻), in the presence of a condensing agent (e.g. trichloroacetonitrile, 2,4,6-trimethylbenzenesulfonyl chloride, 2,4,6-triisopropylbenzenesulfonyl chloride, 2,4,6-trimethylbenzenesulfonylimidazolide, 2,4,6-triisopropylbenzenesulfonyl-3-nitrotriazolide) to give the compound (I).

Process C

Reaction of the compound (VI) with a compound of the formula

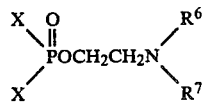 (VII')

wherein X is as defined above, one of R⁶ and R⁷ is identical with the above-mentioned R³ and the other is —COOCH₂C₆H₅, —COOC₆H₅, —CHO, —COCF₃, —COCH₂C₆H₅, —Si(CH₃)₃ or —C(C₆H₅)₃ or R⁶ and R⁷, together with the adjacent nitrogen atom, namely as

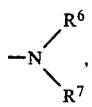

represent

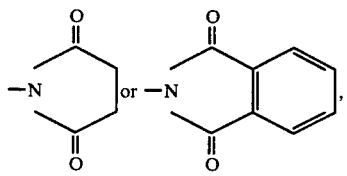

followed by treatment with water and the subsequent deprotection by an appropriate method gives, among the compounds (I), those compounds represented by the formula

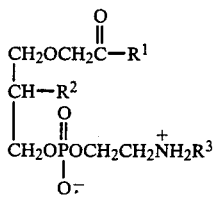 (I')

wherein $R^1$, $R^2$ and $R^3$ are as defined above.

As a derivative of the phosphatidyl choline which is a biomembrane constituent, there is known a compound of the formula

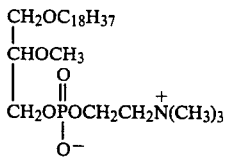 (XIII)

(e.g. Japanese Patent Unexamined Publication No. 134027/1977). Unlike naturally occurring phospholipids, said compound (XIII) is known to have not only antitumor activity but also platelet aggregating activity [D. J. Hanahan et al., Biochem. Biophys. Res. Commun., 99, 183 (1981)]. Such activity against platelets may possibly cause circulatory disorders, such as cerebral thrombosis and angina pectoris.

Moreover, the compound (XIII) shows hypotensive activity and local irritation (necrosis) is also noted. All these activities manifest themselves as toxic effects and therefore are unfavorable for use of the compound (XIII) as a drug.

The present inventors paid their attention to the structure of the fatty acid ester moiety of naturally occurring phospholipids and found that the compounds (I) according to the invention which contain one methylene group between the carbonyl group and the oxygen atom are comparable in antitumor activity to the compound (XIII) but are lacking in the above-mentioned adverse effects.

Furthermore, some of the compounds provided by the invention [e.g. compounds of the formula (I) wherein

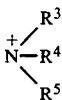

represents a cyclic ammonio group] have platelet activating factor (PAF) antagonizing activity. Such compounds are effective against PAF-induced diseases, such as allergy, circulatory disorders, and shock from a variety of causes.

The compounds (I) according to the invention exhibit marked antitumor and life span prolonging effects in cancerbearing mice, such as mice bearing sarcoma 180, Meth A sarcoma or mouse breast cancer MM46, in a dose of 0.25-2 mg/mouse/day.

Thus, the compounds (I) and salts thereof according to the invention can be used as less toxic antitumor agents in tumor-bearing warm-blooded animals.

For use as antitumor agents, the compounds (I) can be administered safely in the form of various pharmaceutical compositions, such as injections, tablets, capsules, liquid preparations and ointments, either parenterally or orally.

Injections, drip infusions and the like preparations are prepared by the conventional method using, for instance, physiological saline or an aqueous solution containing glucose and other auxiliaries. Tablets, capsules and the like preparations also can be prepared by the conventional method. These preparations are used, as unit dosage forms, by an appropriate route of administration depending on the purpose of administration. Thus, for example, injections are used by the intravenous or subcutaneous route or directly applied to the affected part. The dose of compounds (I) in tumor-bearing warm-blooded animals can be selected depending on the conditions of the patients, route of administration and other factors, generally within the range of about 0.5-150 mg/kg (body weight), preferably about 2-50 mg/kg (body weight). Said pharmaceutical compositions may be administered daily or at 2- to 7-day intervals. It is also possible to administer them 1-3 times daily or by intravenous drip infusion over a prolonged period of time so that the drug concentration in tissues can be maintained at a necessary level for a prolonged period of time.

The compounds (I) and salts thereof exhibit antifungal activity. Said antifungal activity includes antifungal actions against *Trichophyton mentagrophytes, Aspergillus niger, Penicillium citrium, Rhodotolula rubra,* etc. The compounds (I) and salts thereof are therefore useful in the prevention and treatment of diseases caused by such fungi. To the contrary, they are almost inactive to prokaryotic cells.

Antifungal preparations containing the compounds (I) or salts thereof are produced by the conventional method while the active ingredient concentration is not critical, the preparations generally contain the compounds of the invention at a level of about 0.01-70% by weight, preferably about 0.1-5% by weight for the purpose of treating trichophytosis, for instance. The antifungal preparations are administered to diseased parts in the conventional manner once to several times a day, advantageously by coating or spraying.

Furthermore, the compounds (I) are active against phytopathogens, especially phytopathogenic fungi, and are useful as antifungal agents for agricultural use in combating plant diseases such as rice blast (*Pyricularia oryzae*), gray mold (*Botrytia cinerea*) and cirus melanose (*Diaporthe citri*). Preparations containing the antifungal agents can be produced by the conventional method and the active ingredient level is generally and suitably about 10-90% in the case of emulsifiable concentrates, wettable powders and the like, about 0.1-10% in the case of oil solutions, dusts and the like, or about 5-50% in the case of granules. Emulsifiable concentrates and wettable powders, for instance, is preferably diluted to an appropriate extent (e.g. 50-5000 fold) with water, for instance. The antifungal agents for agricultural use may be applied by a variety of per se known methods of application, generally at a dose of about 10-300 g of the active ingredient per 10 ares and desirably at an active ingredient concentration within the range of about 10-1000 ppm.

The following preparation examples, working examples and test examples illustrate the invention in more detail, but they are by no means limitative of the invention.

PREPARATION EXAMPLE 1

3-(2-Oxooctadecyloxy)-2-methoxypropyl 2-trimethylammonioethyl phosphate (80 g) is dissolved in 1.0 liter of distilled water, followed by sterilizing filtration. The filtrate is distributed, in 1-ml portions, into 1000 vials under sterile conditions, followed by lyophilization. Thereafter, the vials are tightly stoppered.

Separately, 2 liters of distilled water for injection which contains 100 g of xylitol or mannitol is sterilely distributed, in 2-ml portions, into 1000 ampules for injection and the ampules are fusedly sealed.

Prior to use, the powder in each former vial is dissolved in the xylitol (or mannitol) solution for injection in each latter ampule.

PREPARATION EXAMPLE 2

Tablets

Tablets each weighing 370 mg and having a diameter of 9.5 mm are produced by the conventional method by blending, for each tablet,
(1) 100 mg of 3-(2-oxooctadecyloxy)-2-methoxypropyl 2-trimethylammonioethyl phosphate,
(2) 200 mg of lactose,
(3) 51 mg of corn starch and
(4) 9 mg of hydroxypropylcellulose,
granulating the mixture, admixing the granules with corn starch (8 mg per tablet) and magnesium stearate (2 mg per tablet) and forming the resulting mixture into tablets.

PREPARATION EXAMPLE 3

The tablets produced in Preparation Example 2 are coated with a solution of hydroxypropylmethylcellulose phtharate (14 mg per tablet) and castor oil (1 mg per tablet) in an acetone-ethanol (4:6) mixture (coating material concentration: 7%), to give enteric coated tablets.

EXAMPLE 1

3-(2-Oxoheptadecyloxy)-2-methoxypropyl 2-trimethylammonioethyl phosphate (1-1) 1,2-Epoxyheptadecane (1)

In 100 ml of dichloromethane was dissolved 26.2 g (0.11 mole) of 1-heptadecene, and a solution of 24.5 g of m-chloroperbenzoic acid in 250 ml of dichloromethane was added dropwise to the solution. The mixture was stirred at room temperature overnight. The resulting crystalline precipitate was filtered off and the filtrate was washed with water, aqueous sodium sulfite, aqueous sodium hydrogen carbonate and aqueous sodium chloride, dried and concentrated. The residue was purified by silica gel column chromatography [eluent: hexane-ethyl acetate (30:1)] to give 16 g of the desired compound as a colorless oil.

IR(film, cm$^{-1}$): 3045, 2925, 2855, 1465, 1420, 1380, 1260, 915, 835, 720

NMR(90 MHz, CDCl$_3$) δ: 0.87(3H), 1.25(26H), 1.47(2H), 2.43(1H), 2.72(1H), 2.88(1H)

(1-2) 3-(2-Hydroxyheptadecyloxy)-2-methoxypropyl tetrahydropyranyl ether (2)

Sodium hydride (50% in oil) (1.74 g, 36.3 mmoles) was washed with n-hexane and dried in a nitrogen gas stream. After addition of 80 ml of dry DMSO, the mixture was heated on a water bath at 70° C. for 30 minutes. When the mixture became homogeneous, 6.9 g (36.3 mmoles) of 2-methylglycerol tetrahydropyranyl ether was added dropwise and, after 15 minutes, 4.62 g (18.2 mmoles) of 1,2-epoxyheptadecane was added dropwise. The mixture was stirred at 70° C. for an hour, poured into 100 ml of broken ice and extracted with 300 ml of n-hexane-ethyl acetate (1:1). The extract was washed with water, dried and concentrated and the residue was purified by silica gel column chromatography to give 4.37 g (53.9%) of the desired compound as a colorless oil.

IR(film, cm$^{-1}$): 3450, 2920, 2850, 1465, 1355, 1200, 1120, 1030, 970, 900, 870, 820

NMR(90 MHz, CDCl$_3$) δ: 0.87(3H, t), 1.25(28H, m), 1.59(6H, m), 2.71(1H, OH), 3.45(3H, s, OCH$_3$), 3.18-4.0(10H, m), 4.62(1H)

(1-3) 3-(2-Oxoheptadecyloxy)-2-methoxypropyl tetrahydropyranyl ether (3)

A mixture of 11.5 g (51.29 mmoles) of pyridinium chlorochromate (PCC) and 4.21 g (51.29 mmoles) of sodium acetate in 70 ml of dichloromethane was stirred, and a solution of 4.37 g (9.80 mmoles) of the above-mentioned alcohol (2) in dichloromethane (35 ml) was added.

The mixture was stirred at room temperature for 2 hours and 4 g of Florisil and 100 ml of ether were added, followed by removal of the supernatant by decantation. The residue was washed with ether and the ether layers were combined and applied to a column of Florisil, followed by elution with ether-methanol (10:1). The eluate was concentrated and the residue was purified by silica gel chromatography [eluent: n-hexane-ethyl acetate (3:1)] to give 4.17 g (95%) of the desired compound as a colorless oil.

IR(film, cm$^{-1}$): 2925, 2850, 1720, 1462, 1350, 1195, 1120, 1075, 1030, 970, 900, 870, 820, 720

NMR(90 MHz, CDCl$_3$) δ: 0.87(3H, t), 1.25(24H, m),

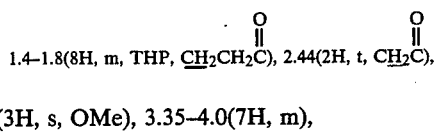

3.47(3H, s, OMe), 3.35-4.0(7H, m),

4.13(2H, s, CCH$_2$O), 4.28(2H, m, POCH$_2$)

TLC: Rf=0.18(CHCl$_3$—CH$_3$OH—H$_2$O 65:25:4)

Elemental analysis. Calcd. for C$_{26}$H$_{54}$NO$_7$P.H$_2$O: C, 57.65; H, 10.42; N, 2.59; P, 5.72. Found: C, 57.36; H, 10.55; N, 2.62; P, 5.76.

EXAMPLE 2

3-(2-Oxoheptadecyloxy)-2-methoxypropyl 2-dimethylaminoethyl phosphate (7)

(2-1)

In 10 ml of toluene containing 2 g of dimethylamine was dissolved 1.5 g of the above crude 3-(2-oxoheptadecyloxy)-2-methoxypropyl 2-bromoethyl phosphate (5) and the solution was stirred at room temperature overnight and then concentrated to dryness. The residue was purified by silica gel chromatography [eluent: (1) methanol and (2) chloroform-methanol-water (65:25:4)] to give 0.83 g (63.2%) of the desired compound as a colorless solid.

IR(KBr, cm$^{-1}$): 3425, 2925, 2855, 1730, 1465, 1230, 1090, 995, 950, 820, 760, 720

NMR(90 MHz, CDCl$_3$) δ: 0.87(3H, t), 1.25(24H, m), 1.60(2H, m),

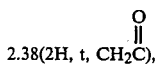

2.38(2H, t, CH$_2$C), 2.70(6H, s, N(CH$_3$)$_2$), 3.06 (2H, m, CH$_2$N), 3.43(3H, s, OCH$_3$), 3.60(3H, m), 3.95(2H, m, CH$_2$OP),

4.12(2H, s, CCH$_2$O), 4.20(2H, m, POCH$_2$)

TLC: Rf=0.30(CHCl$_3$—CH$_3$OH—H$_2$O 65:25:4)

Elemental analysis. Calcd. for C$_{25}$H$_{52}$NO$_7$P.0.5H$_2$O: C, 57.89; H, 10.30; N, 2.70; P, 5.97. Found: C, 57.78; H, 10.33; N, 2.62; P, 5.95.

EXAMPLE 3

3-(2-Oxoheptadecyloxy)-2-methoxypropyl 2-thiazolioethyl phosphate (8)

(3-1)

In 3 ml of toluene was dissolved 0.9 g of the above 3-(2-oxoheptadecyloxy)-2-methoxypropyl 2-bromoethyl phosphate (5), and 1 ml of thiazole was added to the solution. The mixture was stirred at 60° C. for 4 days and then concentrated to dryness. The residue was purified by silica gel chromatography [eluent: (1) methanol and (2) chloroform-methanol-water (65:25:4)] to give 0.20 g of the desired compound.

IR(KBr, cm$^{-1}$): 3425, 2930, 2855, 1730, 1555, 1468, 1240, 1095, 1065, 940, 910, 850, 720,

NMR(90 MHz, CDCl$_3$) δ: 0.87(3H, t), 1.25(24H, m), 1.4–1.7 (2H, m), 2.37(2H, t), 3.39(3H, s), 3.57(3H, m), 3.85(2H, m), 4.15(2H, s), 4.27(2H, m), 4.92(2H, m), 8.33(1H), 8.61(1H), 10.55(1H)

Elemental analysis. Calcd. for C$_{26}$H$_{48}$NO$_7$PS.2H$_2$O: C, 53.32; H, 8.95; N, 2.32; P, 5.29. Found: C, 53.38; H, 9.20; N, 2.54; P, 5.40.

---

4.07(2H, s, CCH$_2$O), 4.60 (1H, THP)

(1-4) 3-(2-Oxoheptadecyloxy)-2-methoxypropanol (4)

In 80 ml of ethanol was dissolved 4.17 g (9.4 mmoles) of the above tetrahydropyranyl ether (3), and 248 mg (0.98 mmoles) of pyridinium p-toluenesulfonate was added. The mixture was stirred at 55° C. for 3 hours. The solvent was distilled off under reduced pressure and the residue was subjected to silica gel chromatography [eluent: n-hexane-ethyl acetate (2:1)] to give 2.9 g (86%) of the desired compound as a colorless wax.

IR(film, cm$^{-1}$): 3410, 2925, 2860, 1730, 1470, 1160, 1120, 1080, 720

NMR(90 MHz, CDCl$_3$) δ: 0.87(3H, t), 1.25(24H, m), 1.60 (2H, m),

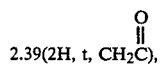

2.39(2H, t, CH$_2$C), 2.70(1H, br. OH), 3.44(3H, s, OCH$_3$), 3.5–3.85(5H, m),

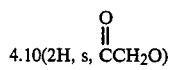

4.10(2H, s, CCH$_2$O)

m.p. 34°–36° C.

(1-5) 3-(2-Oxoheptadecyloxy)-2-methoxypropyl 2-bromoethyl phosphate

In 20 ml of benzene were dissolved 2.5 g (7.35 mmoles of the above alcohol and 3.02 g (12.50 mmoles) of 2-bromoethyl phosphorodichloridate, and 0.99 g of pyridine was added under ice-cooling. The mixture was stirred at room temperature for 5 hours and 20 ml of water was added, followed by vigorous stirring at 80° C. for 40 minutes. After cooling, the solvent was distilled off and the residue was dissolved in ether. This ether solution was washed with water and concentrated to dryness to give 3.90 g of the desired bromo compound (5) as a crude product.

(1-6) 3-(2-Oxoheptadecyloxy)-2-methoxypropyl 2-trimethylammonioethyl phosphate (6)

In 10 ml of toluene containing 2 g of trimethylamine was dissolved 1.5 g of the above bromo compound (5) and the solution was stirred at room temperature for 4 days then concentrated to dryness. The residue was purified by silica gel chromatography [eluent: (1) methanol and (2) chloroform-methanol-water (65:25:4)] to give 0.80 g (57%) of the desired compound as a colorless solid.

IR(KBr, cm$^{-1}$): 3430, 2930, 2860, 1730, 1470, 1240, 1090, 1060, 970, 720

NMR(90 MHz, CDCl$_3$) δ: 0.87(3H, t), 1.25(24H, m), 1.4–1.7 (2H, m),

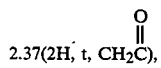

2.37(2H, t, CH$_2$C), 3.33(9H, s, N(CH$_3$)$_3$, 3.42(3H, s, OCH$_3$), 3.58(5H, m), 3.82(4H, m, CH$_2$OP, CH$_2$N),

TLC: Rf=0.21(CHCl₃—CH₃OH—H₂O 65:25:4)

EXAMPLE 4

3-(2-Oxohexadecyloxy)-2-methoxypropyl 2-trimethylammonioethyl phosphate

(4-1) 1,2-Epoxyhexadecane (9)

1-Hexadecene (11.2 g, 50 mmoles) was treated in the same manner as Example 1-1 to give 9.02 g (75%) of the desired epoxide (9).

IR(film, cm⁻¹): 3050, 2930, 2865, 1470, 1415, 1380, 1260, 920, 835, 725

NMR(90 MHz, CDCl₃) δ: 0.87(3H, t), 1.25(24H, m), 1.47(2H, m), 2.43(1H), 2.72(1H), 2.88(1H)

(4-2) 3-(2-Hydroxyhexadecyloxy)-2-methoxypropyl tetrahydropyranyl ether (10)

The epoxide (9) (4.8 g, 20 mmoles) as obtained in Example 4-1 was reacted with 7.6 g (40 mmoles) of 2-methylglycerol monotetrahydropyranyl ether in the same manner as Example 1-2 to give 4.58 g (53.2%) of the desired compound (10).

IR(film, cm⁻¹): 3460, 2930, 2860, 1465, 1355, 1260, 1200, 1120, 1080, 1035, 975, 910, 870, 820, 720

NMR(90 MHz, CDCl₃) δ: 0.87(3H, t), 1.25(26H, m), 1.59(6H, m), 2.69(1H, br. OH), 3.10–4.0(10H, m), 4.58(1H)

(4-3) 3-(2-Oxohexadecyloxy)-2-methoxypropyl tetrahydropyranyl ether (11)

The alcohol (10) (4.58 g, 10.7 mmoles) as obtained in Example 4-2 was reacted with 11.96 g (55.5 mmoles) of pyridinium chlorochromate in the same manner as Example 1-3 to give about 4.5 g of the desired oxo compound (11). The compound was subjected to the next reaction procedure without purification.

(4-4) 3-(2-Oxohexadecyloxy)-2-methoxypropanol (12)

The above oxo compound (11) in 80 ml of ethanol was dissolved, and the detetrahydropyranylation procedure similar to that described in Example 1-4 using pyridinium p-toluenesulfonate was followed to give 3.0 g (82%) of the desired compound (12) as a colorless liquid.

IR(film, cm⁻¹): 3450, 2930, 2860, 1730, 1465, 1120, 1080, 720

NMR(90 MHz, CDCl₃) δ: 0.87(3H, t), 1.25(22H, m), 1.4–1.75 (2H, m),

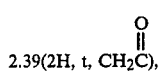

2.78(1H, br. OH), 3.44(3H, s, OCH₃), 3.5–3.8(5H, m),

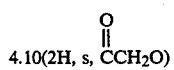

(4-5) 3-(2-Oxohexadecyloxy)-2-methoxypropyl 2-bromoethyl phosphate (13)

The above 3-(2-oxohexadecyloxy)-2-methoxypropanol (12) (2.22 g, 6.5 mmoles) was reacted with 2.80 g (11.6 mmoles) of 2-bromoethyl phosphorodichloridate in the same manner as Example 1-5 to give 3.45 g of the desired bromo compound (13) as a crude product.

(4-6) 3-(2-Oxohexadecyloxy)-2-methoxypropyl 2-trimethylammonioethyl phosphate (14)

In 10 ml of toluene containing 2 g of trimethylamine was dissolved 1.75 g of the above bromo compound (13) and the solution was stirred for 4 days, followed by treatment in the same manner as Example 1-6 to give 1.08 g (66%) of desired compound (14) as a colorless solid.

IR(KBr, cm⁻¹): 3420, 2925, 2855, 1730, 1470, 1240, 1090, 970, 930, 850, 820, 770, 720

NMR(90 MHz, CDCl₃) δ: 0.87(3H, t), 1.25(22H, m), 1.4–1.7 (2H, m),

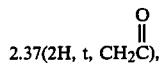

3.33(9H, s, N⁺(CH₃)₃), 3.42(3H, s, OCH₃), 3.57(3H, m), 3.82(4H, m),

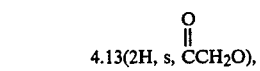

4.23(2H, m, POCH₂)

Elemental analysis. Calcd. for C₂₅H₅₂NO₇P.1.25-H₂O: C, 56.42; H, 10.32; N, 2.63; P, 5.82. Found: C, 56.48; H, 10.58; N, 2.64; P, 5.89.

EXAMPLE 5

(5-1) 3-(2-Oxohexadecyloxy)-2-methoxypropyl 2-dimethylaminoethyl phosphate (15)

The bromo compound (13) (1.7 g) as obtained in Example 4-5 was treated in the same manner as Example 2-1 to give 0.934 g (58%) of the desired compound as a light-yellow solid.

IR(KBr, cm⁻¹): 3430, 2925, 2855, 1730, 1465, 1230, 1090, 995, 950, 820, 760, 720

NMR(90 MHz, CDCl₃) δ: 0.87(3H, t), 1.25(22H, m), 1.4–1.7 (2H, m), 2.38(2H, t), 2.77(6H, s), 3.13(2H, m), 3.43(3H, s), 3.60(3H, m), 3.95(2H, m), 4.11(2H, s), 4.20(2H, m)

Elemental analysis. Calcd. for C₂₄H₅₀NO₇P.H₂O: C, 56.12; H, 10.20; N, 2.73; P, 6.03. Found: C, 55.97; H, 10.16; N, 2.65; P, 6.12.

TLC: Rf=0.29(CHCl₃—CH₃OH—H₂O 65:25:4)

EXAMPLE 6

3-(2-Oxoeicosyloxy)-2-methoxypropyl 2-trimethylammonioethyl phosphate

(6-1) 1,2-Epoxyeicosane (17)

1-Eicosene (21.98 g, 78.5 mmoles) was epoxidized in the same manner as Example 1-1 to give 16.6 g (71%) of the desired compound (17).

IR(KBr, cm⁻¹): 3050, 2925, 2855, 1465, 1382, 1260, 915, 850, 730, 720

NMR(90 MHz, CDCl₃) δ: 0.87(3H), 1.25(32H), 1.47(2H), 2.43 (1H), 2.72(1H), 2.88(1H)

m.p. 39°–40° C.

(6-2) 3-(2-Hydroxyeicosyloxy)-2-methoxypropyl tetrahydropyranyl ether (18)

The above epoxide (17) (4.75 g, 16 mmoles) was reacted with 6.1 g (32 mmoles) of 2-methylglycerol monotetrahydropyranyl ether in the same manner as Example 1-2 to give 4.57 g of the desired compound as a colorless wax.

IR(film, cm$^{-1}$): 3450, 2925, 2855, 1470, 1355, 1200, 1120, 1080, 1030, 970, 905, 870, 820, 720

NMR(90 MHz, CDCl$_3$) δ: 0.87(3H, t), 1.25(34H, m), 1.59(6H, m), 2.69(1H, OH), 3.44(3H, s), 3.11–4.0(10H, m), 4.57(1H)

(6-3) 3-(2-Oxoeicosyloxy)-2-methoxypropyl tetrahydropyranyl ether (19)

The above alcohol compound (18) (4.56 g, 9.74 mmoles) was oxidized under the same conditions in Example 1-3 to give 4.30 g (95%) of the desired compound as a colorless wax.

IR(film, cm$^{-1}$): 2925, 2852, 1720, 1465, 1355, 1200, 1120, 1078, 1030, 970, 900, 870, 818, 720

NMR(90 MHz, CDCl$_3$)δ: 0.87(3H, t), 1.25(30H, m), 1.4–1.8 (8H, m), 2.43(2H, t), 3.47(3H, s), 3.35–4.0(7H, m), 4.07(2H, s), 4.60(1H)

(6-4) 3-(2-Oxoeicosyloxy)-2-methoxypropanol (20)

The above tetrahydropyranyl ether (19) (4.30 g, 9.23 mmoles) was hydrolyzed in the same manner as Example 1-4 to give 3.08 g (87.5%) of the desired compound as a colorless wax.

IR(film, cm$^{-1}$): 3430, 2925, 2855, 1730, 1465, 1380, 1125, 1080, 720

NMR(90 MHz, CDCl$_3$)δ: 0.87(3H, t), 1.25(30H, m), 1.60(2H, m), 2.38(2H, t), 2.55(1H, t, OH), 3.45(3H, s), 3.5–3.85(5H, m), 4.10(2H, s)

m.p. 51°–53° C.

(6-5) 3-(2-Oxoeicosyloxy)-2-methoxypropyl 2-bromoethyl phosphate (21)

The above alcohol (20) (2.3 g, 6.02 mmoles) was reacted with 2.47 g (10.2 mmoles) of 2-bromoethyl phosphorodichloridate in the same manner as Example 1-5 to give 3.60 g of the bromo compound (21) as a crude product.

(6-6) 3-(2-Oxoeicosyloxy)-2-methoxypropyl 2-trimethylammonioethyl phosphate (22)

Using 1.80 g of the above bromo compound (21), the reaction and purification procedure similar to that described in Example 1-6 was followed to give 1.08 g (66%) of the desired compound as a colorless solid.

IR(KBr, cm$^{-1}$): 3425, 2925, 2855, 1730, 1470, 1240, 1090, 1060, 975, 720

NMR(90 MHz, CDCl$_3$)δ: 0.87(3H, t), 1.25(30H, m) 1.4–1.7 (2H, m), 2.37(2H, t), 3.33(9H, s), 3.42(3H, s), 3.58(3H, m), 3.82(4H, m), 4.13(2H, s), 4.28(2H, m)

Elemental analysis. Calcd. for C$_{29}$H$_{60}$NO$_7$P.0.6H$_2$O C, 60.41; H, 10.70; N, 2.43; P, 5.37. Found: C, 60.24; H, 10.91; N, 2.40; P, 5.46.

TLC: RF=0.20(CHCl$_3$—CH$_3$OH—H$_2$O 65:25:4)

EXAMPLE 7

3-(2-Oxooctadecyloxy)-2-methoxypropyl 2-trimethylammonioethyl phosphate

(7-1) 1,2-Epoxyoctadecene (23)

While stirring vigorously 15.12 g (60 mmoles) of 1-octadecene in 300 ml of DMSO containing 2.7 g of water, 21.36 g (120 mmoles) of N-bromosuccinimide was added over a period of 40 minutes. The mixture was stirred at room temperature for 100 minutes, poured into a cold water and extracted with ether. The extract was washed with water, dried and concentrated. The residue was purified by recrystallization and silica gel chromatography to give 10.7 g of 1-bromo-2-hydroxyoctadecane (m.p. 53.5°–54.5° C.), 3.0 g of 2-bromo-1-octadecanol (m.p. 39°–39.5° C.) and 3.78 g of a mixture of these compounds.

In 120 ml of methanol was dissolved 10.7 g (30.7 mmoles) of the above bromohydrin compound, and 16.1 ml (32.2 mmoles) of 2N sodium hydroxide was added. The mixture was stirred at room temperature for an hour. The solvent was then distilled off and the residue was dissolved in n-hexane, washed with water, dried and concentrated. The concentrate was purified by silica gel chromatography to give 7.4 g (90%) of the desired compound (23) as a colorless solid.

IR(film, cm$^{-1}$): 3050, 2930, 2855, 1465, 1260, 920, 835

NMR(60 MHz, CDCl$_3$)δ: 0.87(3H), 1.27(28H), 1.47(2H), 2.45 (1H), 2.73(1H), 2.90(1H)

m.p. 32.5°–33° C.

(7-2) 3-(2-Hydroxyoctadecyloxy)-2-methoxypropyl tetrahydropyranyl ether (24)

The above 1,2-epoxyoctadecane (23) (5.5 g, 20.5 mmoles) was reacted with 7.8 g (41 mmoles) of 2-methylglycerol monotetrahydropyranyl ether in the same manner as Example 1-2 to give 5.1 g (55%) of the desired compound (24) as a colorless wax.

IR(film, cm$^{-1}$): 3350, 2925, 2855, 1470, 1355, 1200, 1120, 1080, 1035, 975

NMR(90 MHz, CDCl$_3$)δ: 0.87(3H, t), 1.27(30H, m), 1.60 (6H, m), 2.68(1H, OH), 3.17–3.95(10H, m), 3.45(3H, s), 4.61(1H)

(7-3) 3-(2-Oxooctadecyloxy)-2-methoxypropyl tetrahydropyranyl ether (25)

The above alcohol (24) (5.1 g, 11.1 mmoles) was oxidized with pyridinium chlorochromate in the same manner as Example 1-3 to give 4.95 g (98%) of the desired oxo compound (25) as a colorless wax.

IR(film, cm$^{-1}$): 2925, 2852, 1720, 1472, 1200, 1120, 1075, 1030

NMR(90 MHz, CDCl$_3$)δ: 0.87(3H, t), 1.25(26H, m), 1.4–1.8 (8H, m), 2.44(2H, t), 3.43(3H, s), 3.35–4.0(7H, m), 4.08(2H, s), 4.60(1H)

(7-4) 3-(2-Oxooctadecyloxy)-2-methoxypropanol (26)

The above oxo compound (25) (4.95 g, 10.8 mmoles) was detetrahydropyranylated in the same manner as Example 1-4 to give 3.33 g (83%) of the desired alcohol (26) as a colorless wax.

IR(film, cm$^{-1}$): 3430, 2920, 2850, 1728, 1465, 1130, 1080, 720

NMR(90 MHz, CDCl$_3$)δ: 0.87(3H, t), 1.24(26H, m), 1.67(2H, m), 2.39(2H, t), 2.6(1H, OH), 3.45(3H, s), 3.5–3.9 (5H, m), 4.10(2H, s)

(7-5) 3-(2-Oxooctadecyloxy)-2-methoxypropyl 2-bromoethyl phosphate (27)

Using 3.33 g (8.95 mmoles) of the above alcohol (26), the procedure similar to that described in Example 1-5 was followed to give 5.23 g of the desired bromo compound (27) as a crude product.

(7-6) 3-(2-Oxooctadecyloxy)-2-methoxypropyl 2-trimethylammonioethyl phosphate (27)

Using 2.61 g of the above bromo compound (26), the reaction and purification procedure similar to that described in Example 1-6 was followed to give 1.65 g 68.8%) of the desired compound (27) as a colorless solid.

IR(KBr, cm$^{-1}$): 3420, 2920, 2852, 1728, 1470, 1235, 1090, 1060, 970

NMR(90 MHz, CDCl$_3$)δ: 0.87(3H, t), 1.25(26H, m), 1.4–1.7 (2H, m), 2.37(2H, t), 3.34(9H, s), 3.41(3H, s), 3.57(3H, m), 3.82(4H, m), 4.13(2H, s), 4.1∝4.4(2H, m)

Elemental analysis. Calcd. for C$_{27}$H$_{56}$NO$_7$P.0.75-H$_2$O: C, 58.83; H, 10.51; N, 2.54; P, 5.61. Found: C, 58.81; H, 10.71; N, 2.48; P, 5.89.

EXAMPLE 8

3-(2-Oxooctadecyloxy)-2-methoxypropyl 2-thiazolioethyl phosphate (28)

Using 2.61 g of the bromo compound (26) as obtained in Example 7-6, the reaction and purification procedure similar to that described in Example 3-1 was followed to give 0.90 g (36%) of the desired compound (28) as a colorless solid.

IR(film, cm$^{-1}$): 3380, 2925, 2860, 1728, 1555, 1470, 1240, 1090, 1060, 940, 910, 762

NMR(90 MHz, CDCl$_3$)δ: 0.87(3H, t), 1.27(26H, m), 1.4–1.7 (2H, m), 2.37(2H, t), 3.39(3H, s), 3.57(3H, m), 3.85(2H, m), 4.15(2H, s), 4.1–4.4(2H, m), 4.92(2H, m), 8.35(1H), 8.63(1H), 10.62(1H)

Elemental analysis. Calcd. for C$_{27}$H$_{50}$NO$_7$PS.H$_2$O: C, 55.75; H, 9.01; N, 2.41; P, 5.32; S, 5.51. Found: C, 55.91; H, 9.28; N, 2.37; P, 5.63; S, 5.48.

EXAMPLE 9

3-(2-Oxoeicosyloxy)-2-methoxypropyl 2-dimethylaminoethyl phosphate (29)

Using 0.90 g of the above bromo compound (21), the reaction procedure similar to that described in Example 2-1 was followed to give 0.43 g of the desired compound (29) as a colorless solid.

IR(KBr, cm$^{-1}$): 2920, 2850, 1730, 1465, 1220, 1085, 995, 945, 815, 760, 720

NMR(90 MHz, CDCl$_3$)δ: 0.87(3H, t), 1.25(30H, m), 1.55 (2H, m), 2.39(2H, t), 2.87(6H, s), 3.23(2H, m), 3.45(3H, s), 3.62(3H, m), 3.97(2H, m), 4.10(2H, s), 4.27(2H, m)

TLC: Rf=0.30 (CHCl$_3$—MeOH—H$_2$O 65:25:4)

Elemental analysis. Calcd. for C$_{28}$H$_{58}$NO$_7$P.0.5H$_2$O: C, 59.97; H, 10.60; N, 2.50; P, 5.52. Found: C, 59.71; H, 10.75; N, 2.54; P, 5.53.

EXAMPLE 10

3-(2-Oxoeicosyloxy)-2-methoxypropyl 2-pyridinioethyl phosphate (30)

In 10 ml of pyridine was dissolved 0.90 g of the above bromo compound (21) and the solution was heated at 40° C. for 40 hours. The reaction mixture was concentrated to dryness and the residue was purified by silica gel chromatography using chloroform-methanol-water (65:25:4) as the eluent to give 0.25 g of the desired compound (30) as a pale yellow solid.

IR(KBr, cm$^{-1}$): 2925, 2855, 1730, 1635, 1470, 1225, 1070

NMR(90 MHz, CDCl$_3$)δ: 0.87(3H, t), 1.25(30H, m), 1.55(2H, m), 2.39(2H, t), 3.45(3H, s), 3.62(3H, m), 3.9(2H, m), 4.10(2H, s), 4.25(2H, m), 5.1(2H, br), 8.1(2H), 8.5(1H), 9.33(2H)

TEST EXAMPLE 1

Antitumor activity of 3-(2-oxooctadecyloxy)-2-methoxypropyl 2-trimethylammonioethyl phosphate (Example 7)

The compound of Example 7 was dissolved in physiological saline and administered to ICR mice (5 animals per group) in a dose of 1 mg/mouse. Four days later, 1×10$^5$ sarcoma 180 cells were inoculated intraperitoneally into each mouse. The life span prolonging ratio T/C between the drug-treated group and control group was 180. The compound (XIII) was administered as a control under the same conditions to give a T/C value of 170.

TEST EXAMPLE 2

Antitumor activity of 3-(2-oxooctadecyloxy)-2-methoxypropyl 2-trimethylammonioethyl phosphate (Example 7)

ICR mice (5 animals per group) were intraperitoneally inoculated with 1×10$^5$ sarcoma 180 cells per mouse. Thereafter, a solution of the compound of Example 7 in physiological saline was administered in a dose of 0.33 mg/mouse three times, namely at hour 1, day 1 and day 2. The life span prolonging ratio as compared with the control (no drug treatment) group was 206.

TEST EXAMPLE 3

Antitumor activity of 3-(2-oxooctadecyloxy)-2-methoxypropyl 2-thiazolioethyl phosphate (Example 8)

The procedure of Test Example 2 was followed using the compound of Example 8 in place of the compound of Example 7. The life span prolonging ratio was 257.

TEST EXAMPLE 4

Antitumor activity of the compound of Example 7

Balb/C mice (5 animals per group) were each subcutaneously inoculated with 1×10$^5$ Meth A sacoma cells. Separately, a solution of the compound of Example 7 in physiological saline was administered to the mice at the site of inoculation in a dose of 0.5 mg/mouse once daily for 5 consecutive days starting from day 1 after tumor cell inoculation. On day 15, the tumor tissues were excised and weighed. The inhibition ratio as compared with the control group was 83%.

TEST EXAMPLE 5

Antitumor activity of the compound of Example 7

CDF$_1$ mice (5 animals per group) were each intraperitoneally inoculated with 1×10$^5$ P388 leukemia cells. Separately, a solution of the compound of Example 7 in physiological saline was intraperitoneally administered to the mice in a dose of 1 mg/mouse once per day for 14 consecutive days starting from day 1 after tumor implantation. The life span prolonging ratio as compared with the control group was 140.

TEST EXAMPLE 6

Antitumor activity of the compound of Example 7

The compound of Example 7 was intraperitoneally administered to C3H/He mice (5 animals per group) in a dose of 0.25 mg/mouse for 4 consecutive days.

On the 5th day, $1 \times 10^4$ MM46 cells were intraperitoneally inoculated into each mouse, and the compound of Example 7 was again administered intraperitoneally to the mice in a dose of 0.25 mg/mouse for 4 days starting from day 1 after inoculation.

The mice in the control group all died within 21 days after tumor implantation, whereas, in the drug-treated group, 4 animals survived on day 46.

TEST EXAMPLE 7

The compounds of Examples 1, 4 and 6 were tested under the same conditions as Test Example 1. The results obtained are shown in Table 1. The value of the number of surviving animals represents the number of animals which survived on the 47th day.

TABLE 1

| Test drug (Example No.) | Life span prolonging ratio (T/C) | Number of surviving animals/ Number of animal tested |
|---|---|---|
| 1 | 290 | 0/5 |
| 4 | 224 | 0/5 |
| 6 | 236 | 1/5 |

TEST EXAMPLE 8

The compounds of Examples 1, 4 and 6 were tested under the same conditions as Test Example 2. The results obtained are shown in Table 1. The value of the number of surviving animals represents the number of animals which survived on the 47th day.

TABLE 2

| Test drug (Example No.) | Life span prolonging ratio (T/C) | Number of surviving animals/ Number of animals tested |
|---|---|---|
| 1 | 340 | 0/5 |
| 4 | 230 | 0/5 |
| 6 | 338 | 0/5 |

TEST EXAMPLE 9

Action on platelets

[Method and results]

A blood sample was taken from a male rabbit using a syringe containing 3.15% citric acid (1 to 9 volumes of blood) as anticoagulant, and centrifuged at 1000 rpm and room temperature for 10 minutes to give platelet rich plasma (PRP). The PRP was further centrifuged at 1400 rpm for 15 minutes. The platelet pellet thus obtained was suspended in $Ca^{++}$-free Tyrode (containing 0.25% of gelatin). A 250 μl portion of the thus-prepared washed PRP was stirred at 37° C. for 2 minutes, then 25 μl of 0.2–0.5 mM $Ca^{++}$ solution was added and the mixture was further stirred for 30 seconds. Thereafter, the test drug was added in an amount sufficient to make a concentration of $3 \times 10^{-5}$M. Platelet aggregation was measured using an aggregation meter (Rigaku Denki). The control compound (XIII) caused 46%–63% aggregation whereas the compounds of Examples 7 and 8 did not cause aggregation at all. The results are shown in Table 3.

TEST EXAMPLE 10

Hypotensive activity

Seven-week-old male Spraugue-Dawley rats (200–290 g) were anesthesized by intraperitoneal administration of 60 mg/kg of pentobarbital sodium and the left carotid artery (for blood pressure measurement) and left femoral vein (for intravenous drug administration) were cannulated. When 300 μg/kg of the control compound (XIII) was administered, a blood pressure fall of 43–75 mmHg was observed, whereas the compounds of Examples 7 and 8 caused no observable blood pressure decrease. The results are shown in Table 3.

TEST EXAMPLE 11

Toxicity testing $LD_{50}$ values were determined in ICR mice by intraperitoneally administering each test compound in the form of a solution in physiological saline. The results are shown in Table 3.

TEST EXAMPLE 12

Local irritation

ICR mice was used and each test compound was subcutaneously administered in a dose of 500 μg/kg. The results are shown in Table 3.

TABLE 3

$$\begin{array}{c} CH_2O\text{---}R \\ | \\ CHOCH_3 \\ | \quad O \\ | \quad \| \\ CH_2OPOCH_2CH_2\overset{+}{X} \\ | \\ O^- \end{array}$$

| Compound (Example No.) | R | $\overset{+}{X}$ | $LD_{50}$ (mg/kg) | Hypotensive action ΔP (mmHg) [duration] | Platelet aggregation | Local irritation |
|---|---|---|---|---|---|---|
| 7 | $\underset{CH_2CC_{16}H_{33}}{\overset{O}{\|}}$ | $-\overset{+}{N}(CH_3)_3$ | >150 | −5 [<30 sec.] | No aggregation | + |
| 8 | $\underset{CH_2CC_{16}H_{33}}{\overset{O}{\|}}$ | 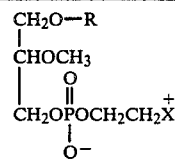 | >150 | −3 [<30 sec.] | No aggregation | ± |
| Control | $C_{18}H_{37}$ | $-\overset{+}{N}(CH_3)_3$ | 25~50 | −43 to −75 [4.5 min.] | 46–63% | +++ |

TEST EXAMPLE 13

Action on cells

The compounds given in Table 4 were tested for microprotozoal growth inhibiting activity (expressed in terms of MIC) in *Tetrahymena pyriformis* W by the liquid dilution method by cultivating said test microorganism in a test medium [20 g of Tryptose peptone (Difco), 1 g of yeast extract, 2 g of glucose, 1000 ml of distilled water, 10 ml of 1M phosphate buffer, pH 7.0] at 28° C. for 44–48 hours. The antiprotozoal activity data obtained are shown in Table 4.

As for the antifungal activity data shown in Table 5, each compound was tested for minimal inhibitory concentrations (MIC) in several typical phytopathogenic fungi used as the test organisms by the serial dilution method using 1% glucose bouillon agar medium.

TABLE 4

MIC (μg/ml) in *Tetrahymena pyriformis*

$$\begin{array}{c} CH_2O-R \\ | \\ CHOCH_3 \\ | \quad O \quad\quad R^3 \\ | \quad \| \quad\quad +/ \\ CH_2OPOCH_2CH_2N-R^4 \\ | \quad\quad\quad\quad\quad \backslash \\ O^- \quad\quad\quad\quad R^5 \end{array}$$

| R | $\begin{array}{c}+/R^3\\-N-R^4\\ \backslash R^5\end{array}$ | MIC |
|---|---|---|
| $C_{18}H_{37}-$ | $-\overset{+}{N}Me_3$ | 1 |
| $C_{16}H_{33}-\overset{O}{\underset{\|}{C}}CH_2-$ | $-\overset{+}{N}Me_3$ | 0.4 |
| $C_{16}H_{33}-\overset{O}{\underset{\|}{C}}-CH_2-$ | 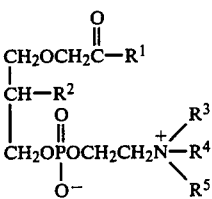 | 1-2 | platelet rich plasma (PRP). The PRP was further centrifuged at 1400 rpm for 15 minutes. The platelet pellet thus obtained was suspended in $Ca^{++}$-free Tyrode (containing 0.25% of gelatin). A 250-μl portion of the thus-prepared washed PRP was stirred at 37° C. for 2 minutes, then 25 μl of 0.2–0.5 mM $Ca^{++}$ solution was added and the mixture was further stirred for 30 seconds. Thereafter, the compound of Example 8 was added to a concentration of $3 \times 10^{-5}$M. Platelet aggregation was measured with an aggregation meter (Rigaku Denki). The activity of the compound of Example 8 as determined in terms of percentage inhibition based on the maximum light transmittance (maximum aggregation) due to PAF in the control PRP was 94%.

We claim:

1. A compound of the formula $$\begin{array}{c} O \\ \| \\ CH_2OCH_2C-R^1 \\ | \\ CH-R^2 \\ | \quad O \quad\quad R^3 \\ | \quad \| \quad\quad +/ \\ CH_2OPOCH_2CH_2N-R^4 \\ | \quad\quad\quad\quad\quad \backslash \\ O^- \quad\quad\quad\quad R^5 \end{array}$$

wherein
$R^1$ is an aliphatic hydrocarbon residue containing 10 to 20 carbon atoms selected from the group consisting of $C_{10-20}$ alkyl, $C_{10-20}$ alkenyl and $C_{10-20}$ alkynyl groups, said groups being unsubstituted or substituted by up to two substituents selected from the group consisting of hydroxy, mercapto, amino, oxo, carbamoyl, halogen, $C_{3-7}$ cycloalkyl and phenyl,
$R^2$ is hydrogen or methoxy, and
$R^3$, $R^4$ and $R^5$ are independently hydrogen or $C_{1-5}$ alkyl,
or a pharmaceutically acceptable salt thereof.

2. A compound of the formula

TABLE 5

Antifungal activity [MIC (μg/ml)]

| R | $\begin{array}{c}+/R^3\\-N-R^4\\ \backslash R^5\end{array}$ | Pyricularia oryzae causative of rice blast | Botrytis cinerea causative of gray mold | Diaporthe citri causative of citrus melanose | Elsinoe fawcetti causative of citrus scab | Cercospora beticola causative of sugar beat leaf spot | Sclerotinia sclerotiorum causative of kidney bean stem rot |
|---|---|---|---|---|---|---|---|
| $C_{18}H_{37}-$ | $-\overset{+}{N}Me_3$ | 6.25 | 25 | — | — | — | >100 |
| $C_{16}H_{33}-\overset{O}{\underset{\|}{C}}-CH_2-$ | $-\overset{+}{N}Me_3$ | 3.12 | 6.25 | 6.25 | 6.25 | 3.12˙ | 25 |
| $C_{16}H_{33}-\overset{O}{\underset{\|}{C}}-CH_2-$ | 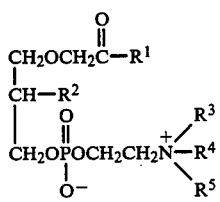 | 3.12 | 100 | 12.5 | 12.5˙ | 12.5 | 25 |

TEST EXAMPLE 14

Anti-PAF activity of the compound of Example 8

[Test method and results]

A blood sample was taken directly from a male rabbit using a syringe containing 3.15% citric acid (1 to 9 volumes of blood) as anticoagulant, and centrifuged at 1000 rpm and room temperature for 10 minutes to give $$\begin{array}{c} O \\ \| \\ CH_2OCH_2C-R^1 \\ | \\ CH-R^2 \\ | \quad O \quad\quad R^3 \\ | \quad \| \quad\quad +/ \\ CH_2OPOCH_2CH_2N-R^4 \\ | \quad\quad\quad\quad\quad \backslash \\ O^- \quad\quad\quad\quad R^5 \end{array}$$

wherein

R¹ is an aliphatic hydrocarbon residue containing 10 to 20 carbon atoms selected from the group consisting of $C_{10-20}$ alkyl, $C_{10-20}$ alkenyl and $C_{10-20}$ alkynyl groups, said groups being unsubstituted or substituted by up to two substituents selected from the group consisting of hydroxy, mercapto, amino, oxo, carbamoyl, halogen, $C_{3-7}$cycloalkyl and phenyl, R² is hydrogen or methoxy, and

represents a cyclic ammonio group,
or a pharmaceutically acceptable salt thereof.

3. A compound according to claim 1, wherein R¹ is $C_{10-20}$ alkyl.

4. A compound according to claim 1, wherein R¹ is an aliphatic hydrocarbon residue containing 14 to 18 carbon atoms.

5. A compound according to claim 1, wherein R¹ is $C_{14-18}$ alkyl.

6. A compound according to claim 1, wherein R² is methoxy.

7. A compound according to claim 2, wherein R¹ is $C_{10-20}$ alkyl.

8. A compound according to claim 2, wherein R¹ is $C_{14-18}$ alkyl.

9. A compound according to claim 2, wherein R² is methoxy.

10. A compound according to claim 2, wherein the cyclic ammonio group is pyridinio, oxazolio, thiazolio, pyridazinio, quinolinio, isoquinolinio, N-$C_{1-4}$ alkylmorpholinio or N-$C_{1-4}$ alkylpiperazinio, each of the said groups being unsubstituted or substituted by $C_{1-4}$ alkyl, hydroxy, hydroxyethyl, aminoethyl, amino, imino, carbamoyl or ureido.

11. A compound according to claim 2, wherein the cyclic ammonio group is pyridinio or thiazolio.

12. 3-(2-Oxoeicosyloxy)-2-methoxypropyl 2-trimethylammonioethyl phosphate.

13. 3-(2-Oxoheptadecyloxy)-2-methoxypropyl 2-thiazolioethyl phosphate.

14. The compound 3-(2-oxoheptadecyloxy)-2-methoxypropyl 2-trimethylammonioethyl phosphate.

15. The compound 3-(2-oxooctadecyloxy)-2-methoxypropyl 2-trimethylammonioethyl phosphate.

16. The compound 3-(21-oxooctadecyloxy)-2-methoxypropyl 2-thiazolioethyl phosphate.

* * * * *